United States Patent
Jahangir Ali et al.

(10) Patent No.: US 10,590,466 B2
(45) Date of Patent: Mar. 17, 2020

(54) PLANT BASED DYE FOR STAINING OF BIOLOGICAL SAMPLES, EXTRACTION METHOD AND USES THEREOF

(71) Applicant: Fathima Benazir Jahangir Ali, Bangalore (IN)

(72) Inventors: Fathima Benazir Jahangir Ali, Bangalore (IN); Alex Dass Paul Rabidass, Bangalore (IN); Handanahal Subbarao Savithri, Bangalore (IN)

(73) Assignee: Fathima Benazir Jahangir Ali, Bangalore (IN)

( * ) Notice: Subject to any disclaimer, the term of this patent is extended or adjusted under 35 U.S.C. 154(b) by 0 days.

(21) Appl. No.: 15/737,929

(22) PCT Filed: Jun. 23, 2016

(86) PCT No.: PCT/IN2016/050196
§ 371 (c)(1),
(2) Date: Dec. 19, 2017

(87) PCT Pub. No.: WO2016/207913
PCT Pub. Date: Dec. 29, 2016

(65) Prior Publication Data
US 2018/0195109 A1    Jul. 12, 2018

(30) Foreign Application Priority Data

Jun. 23, 2015   (IN) .......................... 2080/CHE/2015

(51) Int. Cl.
*C12Q 1/6806* (2018.01)
*C07D 311/94* (2006.01)

(52) U.S. Cl.
CPC .......... *C12Q 1/6806* (2013.01); *C07D 311/94* (2013.01); *C12Q 2563/173* (2013.01)

(58) Field of Classification Search
CPC ...... C07D 311/94; C12Q 1/68; C12Q 1/6806; C12Q 2563/173; A61K 36/48; A61K 2236/00
See application file for complete search history.

(56) References Cited

U.S. PATENT DOCUMENTS

| | | | | |
|---|---|---|---|---|
| 5,753,270 A | * | 5/1998 | Beauchamp | A61K 33/18 424/667 |
| 2002/0061303 A1 | * | 5/2002 | Singh | A61K 31/00 424/94.63 |
| 2008/0279851 A1 | * | 11/2008 | Coyle | C07K 16/2818 424/133.1 |

FOREIGN PATENT DOCUMENTS

| | | | |
|---|---|---|---|
| CN | 102219771 A | 10/2011 | |
| CN | 102241660 A | 11/2011 | |
| CN | 104274489 A | 1/2015 | |
| KR | 20070060714 A | 6/2007 | |
| KR | 20130131508 A | * 12/2013 | |
| WO | 2007/066926 A1 | 6/2007 | |
| WO | WO-2007066928 A1 | * 6/2007 | ............. A61K 36/48 |

OTHER PUBLICATIONS

Bhakta et al., "Interaction of Plant Pigment Brazilin with Synthetic and Natural DNA: Spectroscopic and in silico Perspective," *Interdiscip Sci Computer Life Sci* 5:53-59 (2013).

Rondão et al., "Brazilwood Reds: The (Photo)Chemistry of Brazilin and Brazilein," *J. Phys. Chem. A* 117:10650-10660 (2013).

* cited by examiner

*Primary Examiner* — Sarah Pihonak
(74) *Attorney, Agent, or Firm* — Seed Intellectual Property Law Group LLP

(57) ABSTRACT

The present disclosure provides a composition comprising brazilein which can be used as a fluorescent dye for enhanced visualization of nucleic acids such as DNA, and RNA. Also provided in the specification is a simple, time and cost effective method of extraction of brazilein from bark starting material.

14 Claims, 16 Drawing Sheets

PLANT BASED DYE FOR STAINING OF BIOLOGICAL SAMPLES, EXTRACTION METHOD AND USES THEREOF

FIELD OF INVENTION

The present disclosure relates to the field of reagents for detection of nucleic acids. In particular, the present disclosure provides a composition comprising brazilein for enhanced detection of nucleic acids. Also provided is a fast and cost efficient method of isolation and purification of brazilein.

BACKGROUND OF THE INVENTION

Staining is an important auxiliary technique used in identification, detection, visualization, labeling, targeting, and purification of biological samples. In addition, it is also widely used in microscopy to enhance contrast in the microscopic image. In particular Stains and dyes are frequently used in chemistry, biology and medicine to visualize and quantify nucleic acids, proteins and also other biological materials to highlight structures in the tissues for various reasons such as examining tissues, classifying cell populations, or organelles within individual cells. Stains are chemical compounds that exhibit a detectable response when contacted with a particular target. In the absence of the target, a stain does not exhibit the detectable response. These properties make stains valuable in the detection of the presence or absence of a particular target in a sample. The detectable response can be qualitative or quantitative, depending on the compound, target, and assay parameters.

The detection and quantitation of nucleic acids particularly DNA is a very common task in biotechnological research. Early chemical stains are effective at staining DNA, but also stain RNA. DNA and RNA are often obtained together when isolated from natural sources. Stains that are not selective for DNA make quantitation of the isolated DNA difficult, requiring a purification step to be performed prior to quantitation. Specialized research requires differentiation of different types of nucleic acids like single standard DNA, double standard DNA and plasmid DNA. The nucleic acid screening applications uses presently available toxic and mutagenic fluorescent stains by compromising on safety. The process involves cumbersome safety protocols and expensive disposal practices. In particular, fluorescent stains/dyes are widely used in nucleic acid research to visualize and quantify DNA/RNA fragments in agarose gels. Ethidium bromide (EtBr) has been the predominant dye used for nucleic acid screening for decades because of its low cost and sufficient sensitivity. However, the safety hazard and costs associated with decontamination and waste disposal can ultimately make the dye expensive and unsafe to researchers and environment.

Several alternate stains like SYBR group of stains, Gel red, Gel green, Pico green, Dimeric cyanines etc., have been developed to replace the highly toxic EtBr. Invariably, all these dyes are synthetic-aromatic ring structures highly sensitive to detect nucleic acids. Despite their higher sensitivity they express certain level of toxicity and mutagenicity. The safety claims projected by these dyes are in comparison with the highly toxic EtBr. Thus, there is no safe fluorescent stain available for safe screening of biological samples or nucleic acids.

The compound brazilein is derived from the bark of *Caesalpinia sappan*, a shrub found widely in Asia. Furthermore, the extraction of brazilein through a simple process from *Caesalpinia sappan* species and obtaining a good yield is quite cumbersome and difficult. There are reports on the extraction and separation of brazilin and brazilein compounds from *Caesalpenia* species (WO 2007066926 A1, WO/2007/066926). All these methods explain about the extraction and characterization of brazilein as a food and fabric staining agent. However, the nucleic acid staining property of brazilein in gel based systems and related applications was not attempted. Further, many different methods and strategies have been used in extracting and purifying brazilein compound from the *Caesalpenia* species. In CN102241660 (A), titled "Method for purifying Brazilein", the referred invention explains about an extraction method for brazilein from brazil wood. The invention uses a combination of solvents including ethanol, ethyl ester to extract brazilein. The column purification step followed for the extraction protocol also involves acetonitrile, phosphoric acid as mobile phase and silica gel as filtering medium for eluting brazilein. The method also used preparative HPLC for purifying brazilein from the plant extract. This method is expensive and involves two purifying protocols leading to long and cumbersome procedure.

The invention referred in the patent no CN102219771A titled "Method for extracting brazilein from *sappan* wood", claims a method for extracting brazilein from *sappan* wood. The method involves methanol as a primary solvent for treating raw material followed by macroporous resin based absorption for separating brazilein. Though the method used methanol as the solvent for purifying brazilein, the concentration, solvent combination and incubation duration employed is different, further the method uses several other steps for extraction including, addition of water for dispersion, use of macroporous resin for adsorption, gradient elution using methanol, crystalizing the crystals washing and dissolving the crystals and finally recrystallizing in ethanol and ethyl estate.

In WO 2007066926 A1 titled "a mass production method of brazilein from *Caesalpinia sappan*", the invention claims an alcohol based brazilein extraction method for large scale production. However, the extraction involves two stage crystallization in which alcohol is the only solvent to purify brazilein.

In Korean patent 1020050120665, titled "Rapid and inexpensive mass production method of brazilein having high purity from *Caesalpinia sappan*" discloses a method of extracting brazilein using water or alcohol, however it requires recrystallization and use of controlled conditions and longer incubation periods.

SUMMARY OF THE INVENTION

In an aspect of the present disclosure, there is provided a composition comprising: (a) brazilein (6aS,11bR)-7,11b-Dihydro-6H-indeno[2,1-c]chromene-3,6a,9,10-tetrol); (b) at least one solvent; and (c) at least one compound selected from the group consisting of glycerol, sodium chloride, magnesium sulfate, dimethyl sulfoxide, and combinations thereof.

In an aspect of the present disclosure, there is provided a method of obtaining crystalline brazilein (6aS,11bR)-7,11b-Dihydro-6H-indeno[2,1-c]chromene-3,6a,9,10-tetrol), said method comprising: (a) obtaining bark from *Caesalpinia sappan*; (b) processing said bark to obtain powdered bark; (c) contacting said powdered bark with at least one solvent to obtain a first mixture; (d) subjecting said first mixture to a temperature in the range of 20-90° C. until the volume of the first mixture is reduced by 80-95% to obtain a second mixture; (e) filtering the second mixture to obtain; (i) a filtrate comprising mixture of brazilin and brazilein; and (ii) a residue; and (f) contacting said filtrate to air or at least one oxidizing agent at a temperature in the range of 22-85° C. to evaporate residual solvent to obtain brazilein in crystalline form.

In an aspect of the present disclosure, there is provided a method of detection of nucleic acids in a sample, said method comprising: (i) obtaining a composition comprising: (a) brazilein; (b) at least one solvent; and (c) at least one compound selected from the group consisting of glycerol, sodium chloride, magnesium sulfate, and dimethyl sulfoxide; and (ii) contacting said composition with said sample.

In an aspect of the present disclosure, there is provided a composition comprising: (a) brazilein; (b) at least one solvent; and (c) at least one compound selected from the group consisting of glycerol, sodium chloride, magnesium sulfate, and dimethyl sulfoxide, for use in in-vitro or in-vivo detection of nucleic acids in a sample.

In an aspect of the present disclosure, there is provided a nucleic acid staining kit comprising a composition, said composition comprising: (a) brazilein (6aS,11bR)-7,11b-Dihydro-6H-indeno[2,1-c]chromene-3,6a,9,10-tetrol); (b) at least one solvent; and (c) at least one compound selected from the group consisting of glycerol, sodium chloride, magnesium sulfate, and dimethyl sulfoxide.

In an aspect of the present disclosure, there is provided brazilein for use in in-vitro or in-vivo detection of nucleic acids in a sample.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

FIG. 4a-d depicts the electrophoresis results of various nucleic acids such as plasmid DNA (a), genomic DNA (b), ss DNA(c), and RNA(d) stained with indicating the effectiveness of brazilein in staining different types of nucleic acids, in accordance with an embodiment of the present disclosure.

Figure 5A:
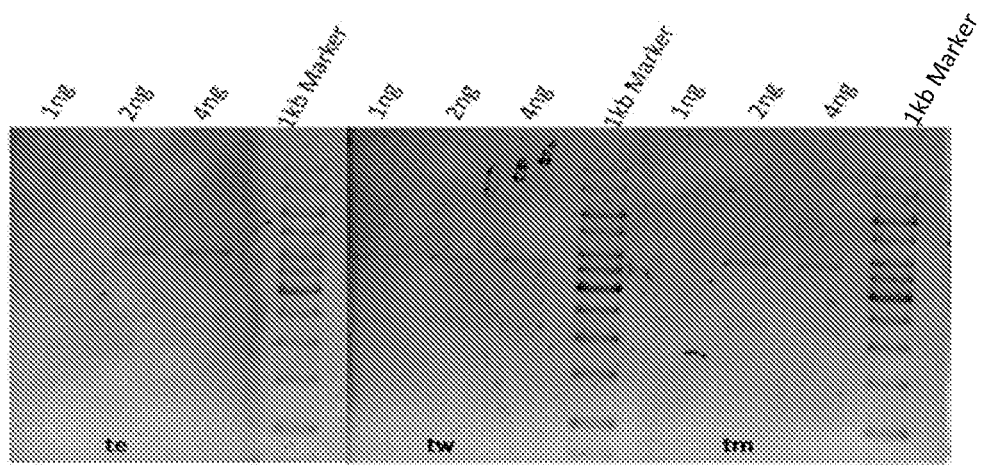

FIG. 5a depicts the capability of three brazilein extracts (tm-methanol, te-ethanol and tw-water) to detect concentrations of DNA as low as 1 ng, in accordance with an embodiment of the present disclosure.

Figure 5B:
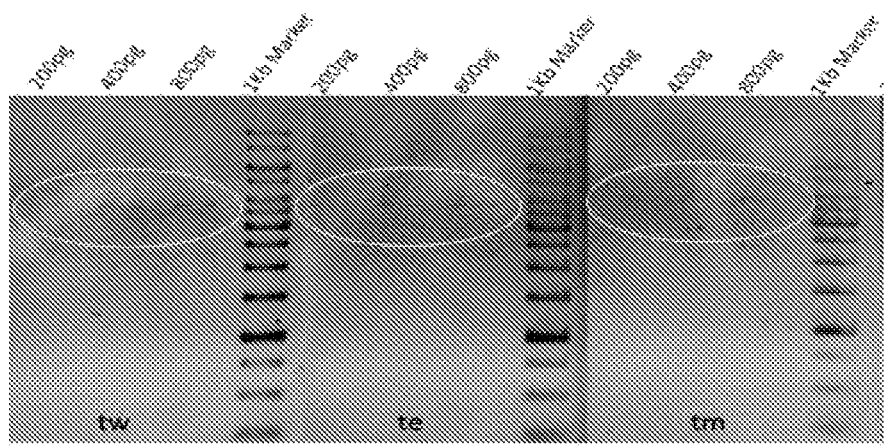

FIG. 5b depicts the capability of three brazilein extracts (tm-methanol, te-ethanol and tw-water) to detect concentrations of DNA as low as 400 pg, in accordance with an embodiment of the present disclosure.

Figure 6A:
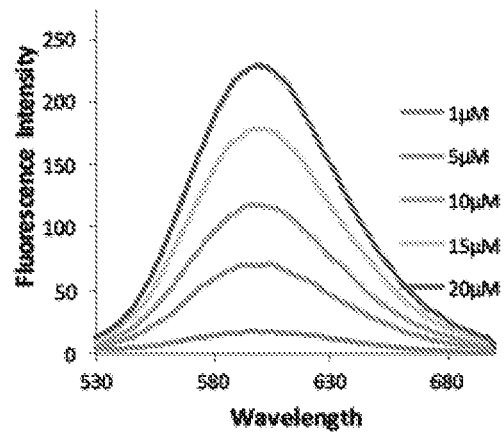

FIG. 6a depicts the concentration dependent fluorescence spectra of ethidium bromide compared to equivalent concentration of methanolic (tm) or ethanolic (te) extract of brazilein, in accordance with an embodiment of the present disclosure.

Figure 6B:
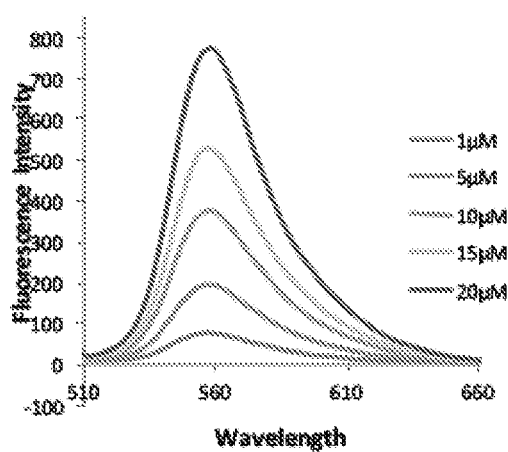

FIG. 6b depicts the concentration dependent fluorescence spectra of ethidium bromide, in accordance with an embodiment of the present disclosure.

Figure 6C:
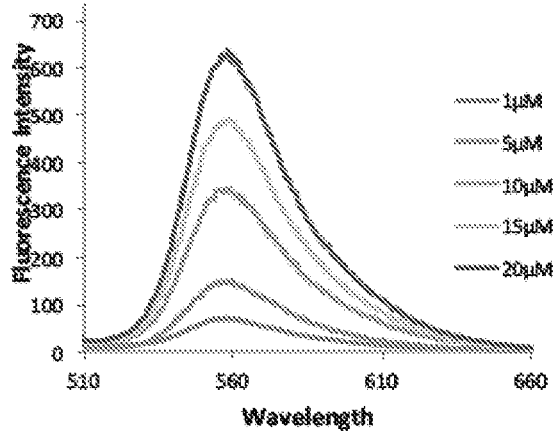

FIG. 6c depicts the concentration dependent fluorescence spectra of methanolic extract of brazilein, in accordance with an embodiment of the present disclosure.

Figure 7A:
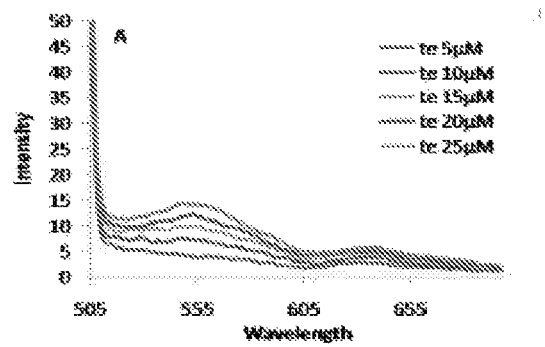

FIG. 7a depicts the effect of pH 5 on fluorescence of brazilein at various concentrations, in accordance with an embodiment of the present disclosure.

Figure 7B:
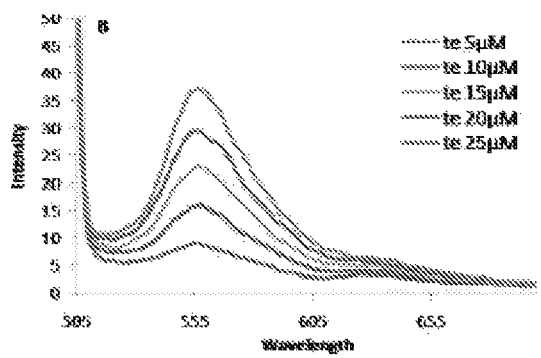

FIG. 7b depicts the effect of pH 6 on fluorescence of brazilein at various concentrations, in accordance with an embodiment of the present disclosure.

Figure 7C:
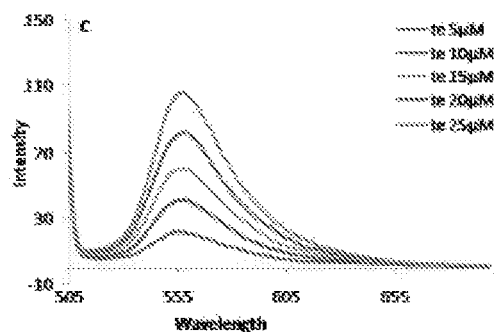

FIG. 7c depicts the effect of pH 7 on fluorescence of brazilein at various concentrations, in accordance with an embodiment of the present disclosure.

Figure 7D:
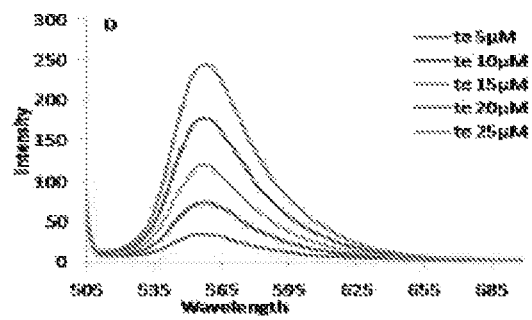

FIG. 7d depicts the effect of pH 8 on fluorescence of brazilein at various concentrations, in accordance with an embodiment of the present disclosure.

Figure 7E:
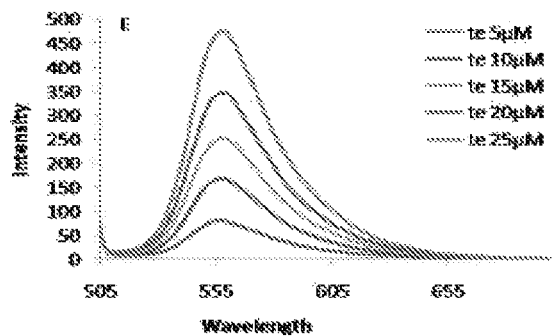

FIG. 7e depicts the effect of pH 9 on fluorescence of brazilein at various concentrations, in accordance with an embodiment of the present disclosure.

Figure 7F:
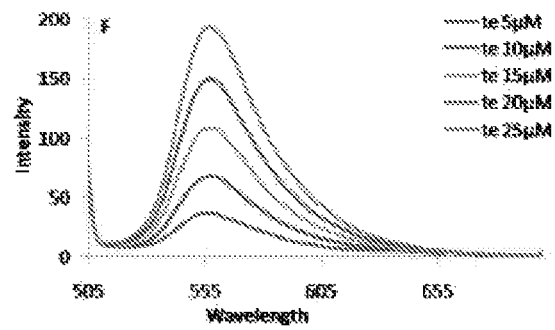

FIG. 7f depicts the effect of pH 10 on fluorescence of brazilein at various concentrations, in accordance with an embodiment of the present disclosure.

Figure 8:
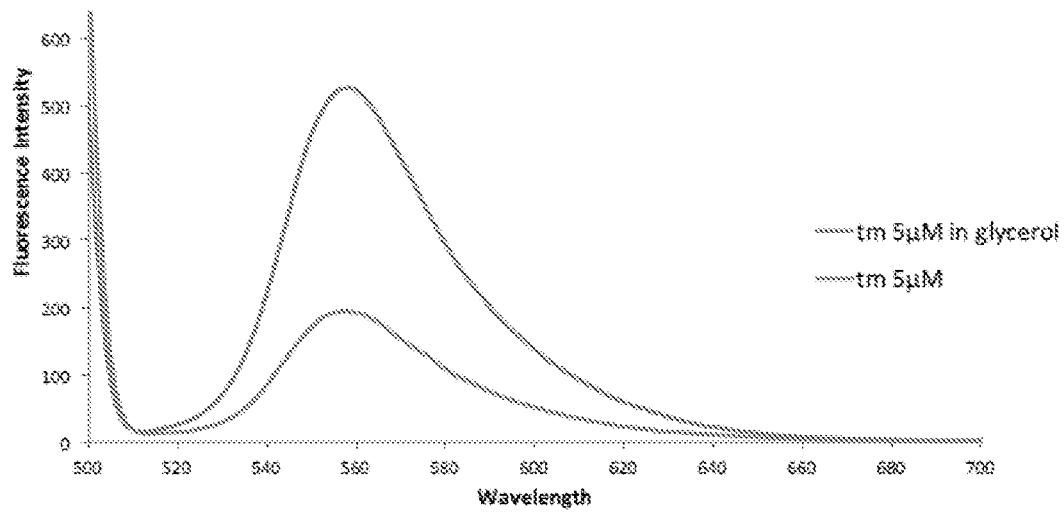

FIG. 8 depicts the fluorescence spectra image depicting the enhanced effect on fluorescence on addition of glycerol to brazilein, in accordance with an embodiment of the present disclosure.

Figure 9:
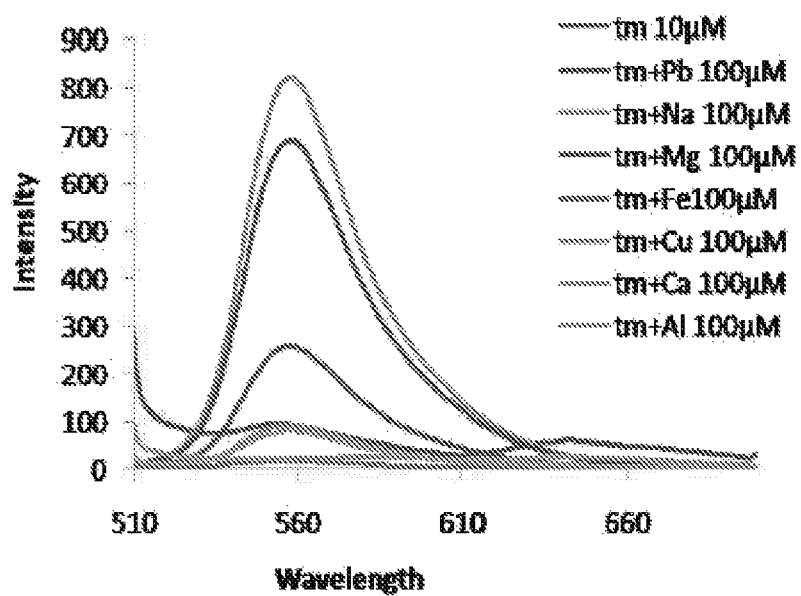

FIG. 9 depicts the effect of various metal ions on fluorescent intensity of methanolic extract of brazilein, in accordance with an embodiment of the present disclosure.

Figure 10:
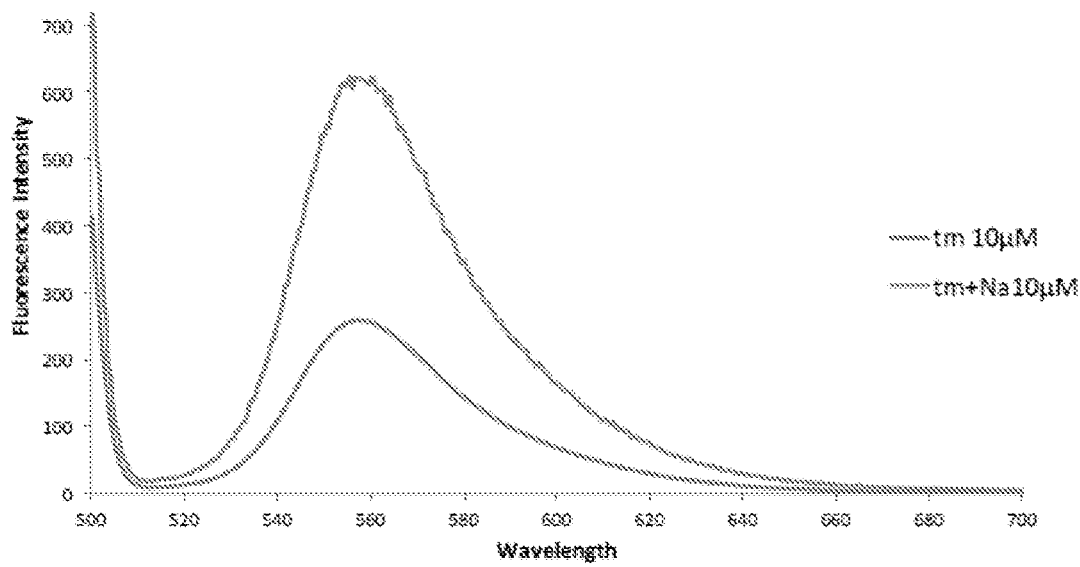

FIG. 10 depicts the fluorescence spectra image depicting the enhanced effect on fluorescence on addition of sodium chloride to brazilein, in accordance with an embodiment of the present disclosure.

Figure 11:
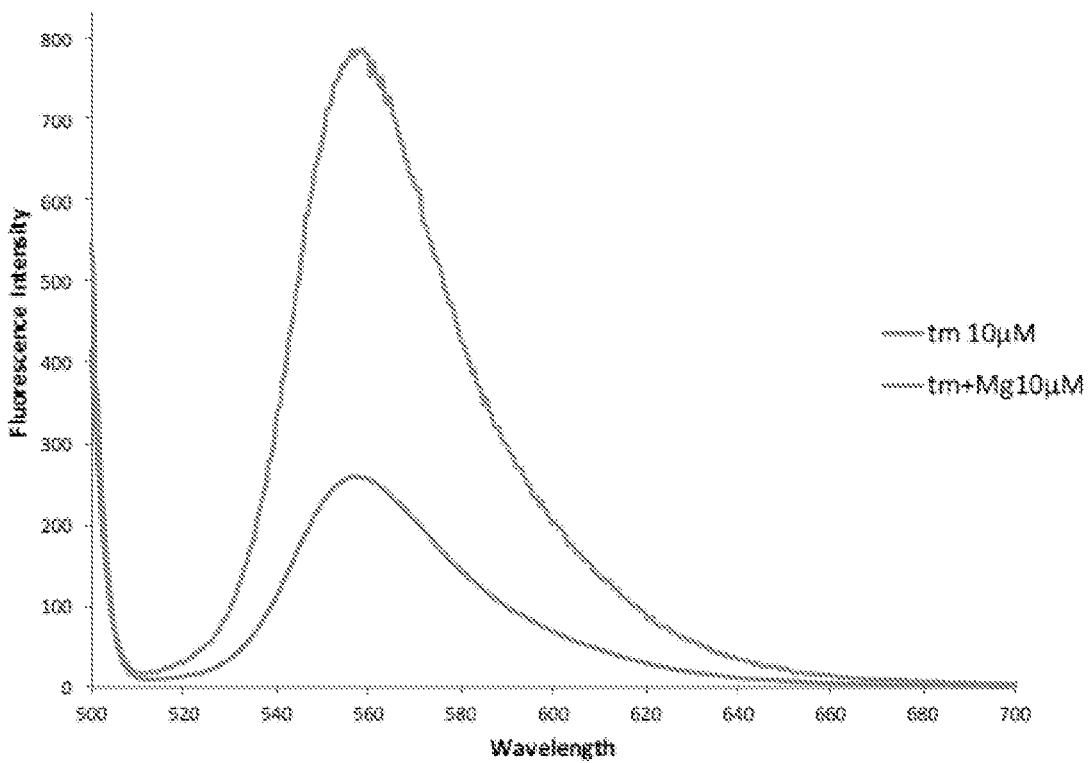

FIG. 11 depicts the fluorescence spectra image depicting enhanced effect on fluorescence on addition of magnesium sulfate to brazilein, in accordance with an embodiment of the present disclosure.

Figure 12A:
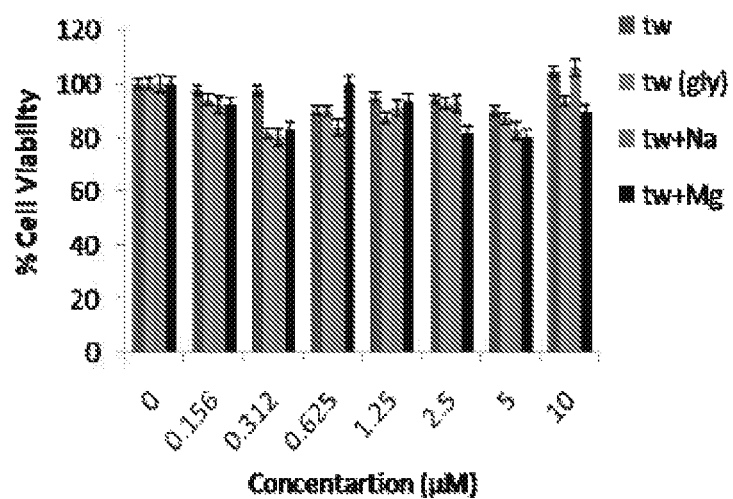

FIG. 12a depicts the cell viability of HeLa cells upon exposure to varying concentrations of a various compositions comprising water extract of brazilein, in accordance with an embodiment of the present disclosure.

Figure 12B:
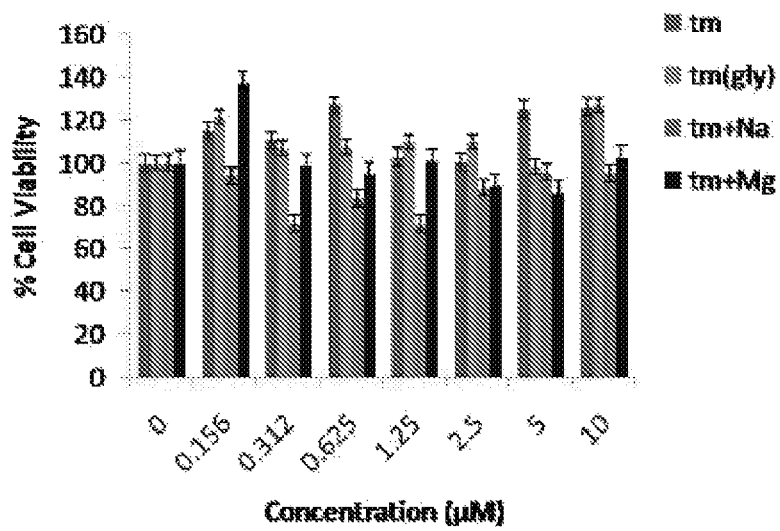

FIG. 12b depicts the cell viability of HeLa cells upon exposure to varying concentrations of a various compositions comprising methanolic extract of brazilein, in accordance with an embodiment of the present disclosure.

Figure 13:
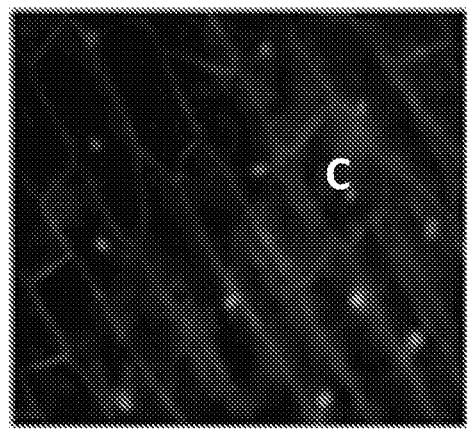

FIG. 13 depicts the staining of onion epidermal cells nucleus by brazilein, in accordance with an embodiment of the present disclosure.

Figure 14A:
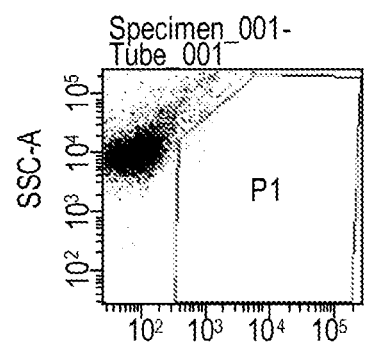

FIG. 14a depicts the FACS analysis of control cells without brazilein, in accordance with an embodiment of the present disclosure.

Figure 14B:
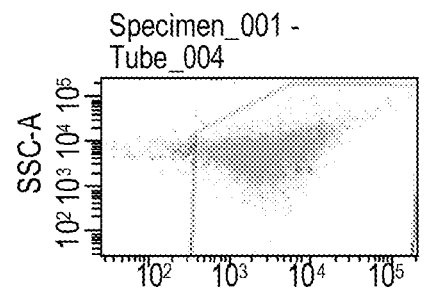

FIG. 14b depicts the efficacy of brazilein uptake by live cells as ascertained by FACS analysis, in accordance with an embodiment of the present disclosure.

Figure 15:
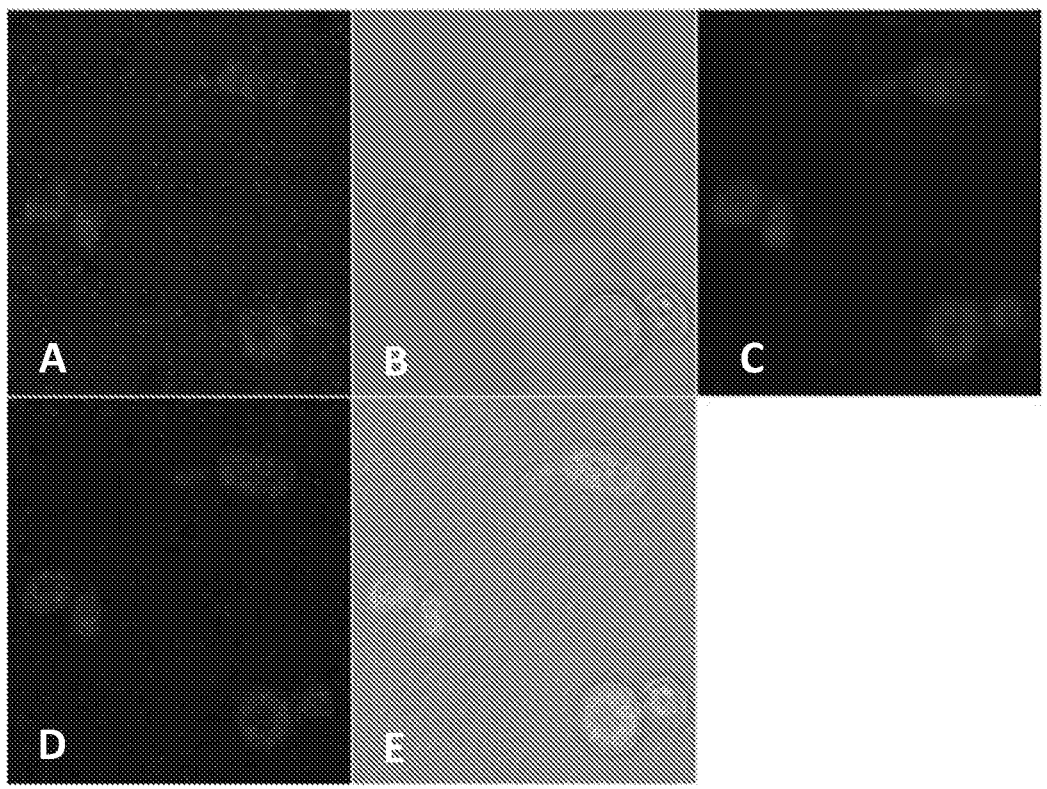

FIG. 15a depicts the visualization of nucleus in live cells (green filter) upon addition of brazilein, in accordance with an embodiment of the present disclosure.

FIG. 15b depicts the phase contrast image of live yeast cells, in accordance with an embodiment of the present disclosure.

FIG. 15c depict the visualization of nucleus in live cells (red filter) upon addition of brazilein, in accordance with an embodiment of the present disclosure.

FIG. 15d depicts the visualization of nucleus in live cells (far red filter) upon addition of brazilein, in accordance with an embodiment of the present disclosure.

FIG. 15e depicts the merged image of FIGS. 15a-d, in accordance with an embodiment of the present disclosure.

Figure 16:
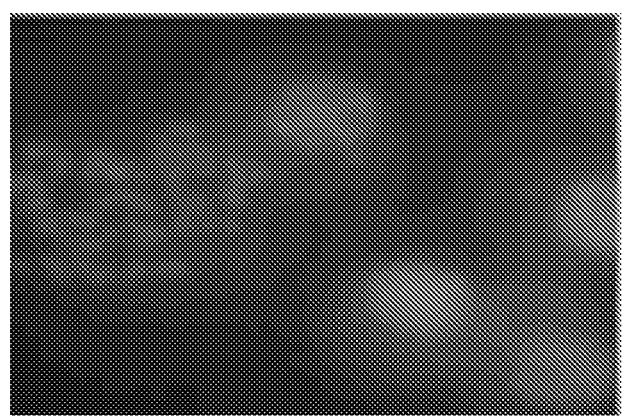

FIG. 16 depicts the FISH image using brazilein as a DNA dye, in accordance with an embodiment of the present disclosure.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The term "ssDNA" refers to single stranded DNA.

The term "ssRNA" refers to single stranded RNA.

The term "tm" can be used interchangeably with methanolic extract of brazilein.

The term "tw" can be used interchangeably with water extract of brazilein.

The term "te" can be used interchangeably with ethanolic extract of brazilein.

The term "EtBr" refers to ethidium bromide, and can be used interchangeably.

A composition comprising "synergistic activity" or a "synergistic composition" is a combination of compounds which exhibits increased biological or functional activity as a non-linear multiple of the biological or functional activity of the individual compounds. In other words, the combined biological or functional activity of two or more compounds being tested is significantly greater than the expected result based on independent effects of the compounds when tested separately. Synergy may be apparent only at some ranges or concentrations. Also the synergistic combination of the compounds may be different for different kinds of biological effects being tested.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure, as described herein.

In an embodiment of the present disclosure, there is provided a composition comprising: (a) brazilein (6aS, 11bR)-7,11b-Dihydro-6H-indeno[2,1-c]chromene-3,6a,9, 10-tetrol); (b) at least one solvent; and (c) at least one compound selected from the group consisting of glycerol, sodium chloride, magnesium sulfate, dimethyl sulfoxide, and combinations thereof.

In an embodiment of the present disclosure, there is provided a composition as described herein, wherein brazilein weight percentage in said composition is in the range of 0.000284-0.0284%.

In an embodiment of the present disclosure, there is provided a composition as described herein, wherein brazilein concentration in said composition is in the range of 10 µM-1 mM.

In an embodiment of the present disclosure, there is provided a composition as described herein, wherein brazilein weight percentage in said composition is 0.0284%.

In an embodiment of the present disclosure, there is provided a composition as described herein, wherein brazilein concentration in said composition is 1 mM.

In an embodiment of the present disclosure, there is provided a composition a described herein, herein said solvent is selected from the group consisting of water, methanol, ethanol, acetone, and combinations thereof.

In an embodiment of the present disclosure, there is provided a composition as described herein, wherein said solvent weight percentage in said composition is in quantity sufficient to dissolve brazilein.

In an embodiment of the present disclosure, there is provided a composition as described herein, wherein said compound is sodium chloride.

In an embodiment of the present disclosure, there is provided a composition as described herein, wherein said compound is magnesium sulfate.

In an embodiment of the present disclosure, there is provided a composition as described herein, wherein said compound is glycerol.

In an embodiment of the present disclosure, there is provided a composition as described herein, wherein said compound is dimethyl sulfoxide (DMSO).

In an embodiment of the present disclosure, there is provided a composition as described herein, wherein brazilein to sodium chloride w/w ratio in said composition is in the range of 1:0.0035-1:3.52.

In an embodiment of the present disclosure, there is provided a composition as described herein, wherein sodium chloride weight percentage in said composition is in the range of 0.0001-0.001%.

In an embodiment of the present disclosure, there is provided a composition as described herein, wherein sodium chloride weight percentage in said composition is 0.001%.

In an embodiment of the present disclosure, there is provided a composition a described herein, wherein brazilein to sodium chloride w/w ratio in said composition is 1:0.352.

In an embodiment of the present disclosure, there is provided a composition as described herein, wherein brazilein weight percentage in said composition is 0.0284% and sodium chloride weight percentage in said composition is 0.001%.

In an embodiment of the present disclosure, there is provided a composition as described herein, wherein brazilein to magnesium sulfate w/w ratio in said composition is in the range of 1:0.0035-1:3.52.

In an embodiment of the present disclosure, there is provided a composition as described herein, wherein magnesium chloride weight percentage in said composition is in the range of 0.0001-0.001%.

In an embodiment of the present disclosure, there is provided a composition as described herein, wherein magnesium chloride weight percentage in said composition is 0.001%.

In an embodiment of the present disclosure, there is provided a composition a described herein, wherein brazilein to magnesium sulfate w/w ratio in said composition is 1:0.352.

In an embodiment of the present disclosure, there is provided a composition a described herein, wherein brazilein weight percentage in said composition is 0.0284% and magnesium sulfate weight percentage in said composition is 0.001%.

In an embodiment of the present disclosure, there is provided a composition as described herein, wherein brazilein to glycerol w/w ratio in said composition is in the range of 1:887-1:133098.

In an embodiment of the present disclosure, there is provided a composition as described herein, wherein glycerol weight percentage in said composition is in the range of 25.2-37.8%.

In an embodiment of the present disclosure, there is provided a composition as described herein, wherein glycerol weight percentage in said composition is 25.2%.

In an embodiment of the present disclosure, there is provided a composition as described herein, wherein glycerol weight percentage in said composition is 37.8%.

In an embodiment of the present disclosure, there is provided a composition as described herein, wherein brazilein to glycerol w/w ratio in said composition is 1:887.3.

In an embodiment of the present disclosure, there is provided a composition as described herein, wherein brazilein to glycerol w/w ratio in said composition is 1:1330.9.

In an embodiment of the present disclosure, there is provided a composition as described herein, wherein brazilein weight percentage in said composition is 0.0284% and glycerol weight percentage in said composition is 25.2%.

In an embodiment of the present disclosure, there is provided a composition as described herein, wherein brazilein weight percentage in said composition is 0.0284% and glycerol weight percentage in said composition is 37.8%.

In an embodiment of the present disclosure, there is provided a composition as described herein, wherein brazilein to dimethyl sulfoxide w/w ratio in said composition is in the range of 1:2464-1:316901.

In an embodiment of the present disclosure, there is provided a composition as described herein, wherein DMSO weight percentage in said composition is in the range of 70-90%.

In an embodiment of the present disclosure, there is provided a composition as described herein, wherein DMSO weight percentage in said composition is 70%.

In an embodiment of the present disclosure, there is provided a composition as described herein, wherein DMSO weight percentage in said composition is 90%.

In an embodiment of the present disclosure, there is provided a composition as described herein, wherein brazilein to dimethyl sulfoxide w/w ratio in said composition is 1:2464.7.

In an embodiment of the present disclosure, there is provided a composition as described herein, wherein brazilein to dimethyl sulfoxide w/w ratio in said composition is 1:3169.

In an embodiment of the present disclosure, there is provided a composition as described herein, wherein brazilein weight percentage in said composition is 0.0284% and DMSO weight percentage in said composition is 70%.

In an embodiment of the present disclosure, there is provided a composition as described herein, wherein brazilein weight percentage in said composition is 0.0284% and DMSO weight percentage in said composition is 90%.

In an embodiment of the present disclosure, there is provided a method of obtaining crystalline brazilein (6aS,11bR)-7,11b-Dihydro-6H-indeno[2,1-c]chromene-3,6a,9,10-tetrol), said method comprising the steps of: (a) obtaining bark from *Caesalpinia sappan*; (b) processing said bark to obtain powdered bark; (c) contacting said powdered bark with at least one solvent to obtain a first mixture; (d) subjecting said first mixture to a temperature in the range of 20-90° C. until the volume of the first mixture is reduced by 80-95% to obtain a second mixture; (e) filtering the second mixture to obtain (i) a filtrate comprising mixture of brazilin and brazilein; and (ii) a residue; and (f) contacting said filtrate to air or at least one oxidizing agent at a temperature in the range of 22-85° C. to evaporate residual solvent to obtain brazilein in crystalline form.

In an embodiment of the present disclosure, there is provided a method of obtaining crystalline brazilein as described herein, wherein bark from *C. sappan* moisture content is in the range of 5-15%.

In an embodiment of the present disclosure, there is provided a method of obtaining crystalline brazilein as described herein, wherein bark from *C. sappan* moisture content is in the range of 5-14%.

In an embodiment of the present disclosure, there is provided a method of obtaining crystalline brazilein as described herein, wherein bark from *C. sappan* moisture content is in the range of 5-12%.

In an embodiment of the present disclosure, there is provided a method of obtaining crystalline brazilein as described herein, wherein bark from *C. sappan* moisture content is in the range of 5-10%.

In an embodiment of the present disclosure, there is provided a method of obtaining crystalline brazilein as described herein, wherein bark from *C. sappan* moisture content is in the range of 5-8%.

In an embodiment of the present disclosure, there is provided a method of obtaining crystalline brazilein as described herein, wherein bark from *C. sappan* moisture content is in the range of 5-6%.

In an embodiment of the present disclosure, there is provided a method of obtaining crystalline brazilein as described herein, wherein said solvent is selected from the group consisting of water, methanol, ethanol, acetone, and combinations thereof.

In an embodiment of the present disclosure, there is provided a method of obtaining crystalline brazilein as described herein, wherein said solvent is water.

In an embodiment of the present disclosure, there is provided a method of obtaining crystalline brazilein as described herein, wherein said solvent is ethanol.

In an embodiment of the present disclosure, there is provided a method of obtaining crystalline brazilein as described herein, wherein said solvent is methanol.

In an embodiment of the present disclosure, there is provided a method of obtaining crystalline brazilein as described herein, wherein said solvent is acetone.

In an embodiment of the present disclosure, there is provided a method of obtaining crystalline brazilein as described herein, wherein said solvent is a combination of methanol and ethanol.

In an embodiment of the present disclosure, there is provided a method of obtaining crystalline brazilein as described herein, wherein said solvent is a combination of methanol and ethanol at v/v ratio of 1:1.

In an embodiment of the present disclosure, there is provided a method of obtaining crystalline brazilein as described herein, wherein said solvent is a combination of methanol and water.

In an embodiment of the present disclosure, there is provided a method of obtaining crystalline brazilein as described herein, wherein said solvent is a combination of methanol and water at v/v ratio of 4:1.

In an embodiment of the present disclosure, there is provided a method of obtaining crystalline brazilein as described herein, wherein said solvent is a combination of ethanol and water.

In an embodiment of the present disclosure, there is provided a method of obtaining crystalline brazilein as described herein, wherein said solvent is a combination of ethanol and water at v/v ratio of 4:1.

In an embodiment of the present disclosure, there is provided a method of obtaining crystalline brazilein as described herein, wherein said solvent is a combination of methanol and acetone.

In an embodiment of the present disclosure, there is provided a method of obtaining crystalline brazilein as described herein, wherein said solvent is a combination of methanol and acetone at v/v ratio of 1:1.

In an embodiment of the present disclosure, there is provided a method of obtaining crystalline brazilein as described herein, wherein said solvent is a combination of acetone and water.

In an embodiment of the present disclosure, there is provided a method of obtaining crystalline brazilein as described herein, wherein said solvent is a combination of acetone and water at v/v ratio of 1:1.

In an embodiment of the present disclosure, there is provided a method of obtaining crystalline brazilein as described herein, wherein in step (c), powdered bark to solvent w/w ratio in said first mixture is in the range of 1:5-1:20.

In an embodiment of the present disclosure, there is provided a method of obtaining crystalline brazilein as described herein, wherein in step (c), powdered bark to solvent w/w ratio in said first mixture is 1:20.

In an embodiment of the present disclosure, there is provided a method of obtaining crystalline brazilein as described herein, wherein in step (c), powdered bark amount is 5 g and solvent volume is 100 ml.

In an embodiment of the present disclosure, there is provided a method of obtaining crystalline brazilein as described herein, wherein step (c) optionally further comprises contacting at least one oxidizing agent to the first mixture.

In an embodiment of the present disclosure, there is provided a method of obtaining crystalline brazilein as described herein, wherein step (c) further comprises contacting at least one oxidizing agent to the first mixture.

In an embodiment of the present disclosure, there is provided a method of obtaining crystalline brazilein (6aS, 11bR)-7,11b-Dihydro-6H-indeno[2,1-c]chromene-3,6a,9,10-tetrol), said method comprising the steps of: (a) obtaining bark from *Caesalpinia sappan*; (b) processing said bark to obtain powdered bark; (c) contacting said powdered bark with at least one solvent, and at least one oxidizing agent to obtain a first mixture; (d) subjecting said first mixture to a temperature in the range of 20-90° C. until the volume of the first mixture is reduced by 80-95% to obtain a second mixture; (e) filtering the second mixture to obtain (i) a filtrate comprising mixture of brazilin and brazilein; and (ii) a residue; and (f) contacting said filtrate to air or at least one oxidizing agent at a temperature in the range of 22-85° C. to evaporate residual solvent to obtain brazilein in crystalline form.

In an embodiment of the present disclosure, there is provided a method of obtaining crystalline brazilein as described herein, wherein said oxidizing agent is acetone.

In an embodiment of the present disclosure, there is provided a method of obtaining crystalline brazilein as described herein, wherein said residue from step (e)(ii) is subjected to repeated extraction comprising the steps of: (a) contacting said residue with at least one solvent to obtain a third mixture; (b) subjecting the third mixture to a temperature in the range of 20-90° C. until the volume of the first mixture is reduced by 80-95% to obtain a fourth mixture; (c) filtering the fourth mixture to obtain: (i) a filtrate comprising mixture of brazilin and brazilein; and (ii) a residue; (d) contacting said filtrate to air or at least one oxidizing agent at a temperature in the range of 22-85° C. to evaporate residual solvent to obtain brazilein in crystalline form.

In an embodiment of the present disclosure, there is provided a method of obtaining crystalline brazilein as described herein, wherein said repeated extraction process is carried out for 3-5 cycles.

In an embodiment of the present disclosure, there is provided a method of obtaining crystalline brazilein as described herein, wherein said repeated extraction process is carried out for 3 cycles.

In an embodiment of the present disclosure, there is provided a method of obtaining crystalline brazilein as described herein, wherein said repeated extraction process is carried out for 4 cycles.

In an embodiment of the present disclosure, there is provided a method of obtaining crystalline brazilein as described herein, wherein said repeated extraction process is carried out for 5 cycles.

In an embodiment of the present disclosure, there is provided a method of obtaining crystalline brazilein, said method comprising: (a) obtaining bark from *Caesalpinia sappan*; (b) processing said bark to obtain powdered bark; (c) contacting said powdered bark with at least one solvent to obtain a first mixture; (d) subjecting said first mixture to a temperature in the range of 20-90° C. until the volume of the first mixture is reduced by 80-95% to obtain a second mixture; (e) filtering the second mixture to obtain (i) a filtrate comprising mixture of brazilin and brazilein; and (ii) a residue; (f) subjecting the residue to 3-5 cycles of extraction of steps (c) through (i); (g) pooling the filtrate from each extraction cycle; and (f) contacting said filtrate to air or at least one oxidizing agent at a temperature in the range of 22-85° C. to evaporate residual solvent to obtain brazilein in crystalline form.

In an embodiment of the present disclosure, there is provided a method of obtaining crystalline brazilein as described herein, wherein said method yields 15-30 g of crystalline brazilein per 100 gram of said powdered bark.

In an embodiment of the present disclosure, there is provided a method of obtaining crystalline brazilein as described herein, wherein said method yields 20 g brazilein per 100 g powdered bark, and said solvent is methanol.

In an embodiment of the present disclosure, there is provided a method of obtaining crystalline brazilein as described herein, wherein said method yields 21.5 g brazilein per 100 g powdered bark, and said solvent is methanol and ethanol at 1:1 v/v ratio.

In an embodiment of the present disclosure, there is provided a method of obtaining crystalline brazilein as described herein, wherein said method yields 19 g brazilein per 100 g powdered bark, and said solvent is methanol and water at 4:1 v/v ratio.

In an embodiment of the present disclosure, there is provided a method of obtaining crystalline brazilein as described herein, wherein said method yields 22 g brazilein per 100 g powdered bark, and said solvent is ethanol and water at 4:1 v/v ratio.

In an embodiment of the present disclosure, there is provided a method of obtaining crystalline brazilein as described herein, wherein said method yields 18 g brazilein per 100 g powdered bark, and said solvent is water.

In an embodiment of the present disclosure, there is provided a method of obtaining crystalline brazilein as described herein, wherein said method yields 25 g brazilein per 100 g powdered bark, and said solvent is ethanol.

In an embodiment of the present disclosure, there is provided a method of obtaining crystalline brazilein as described herein, wherein said method yields 28.5 g brazilein per 100 g powdered bark, and said solvent is acetone.

In an embodiment of the present disclosure, there is provided a method of obtaining crystalline brazilein as described herein, wherein said method yields 25 g brazilein per 100 g powdered bark, and said solvent is methanol and acetone at 1:1 v/v ratio.

In an embodiment of the present disclosure, there is provided a method of obtaining crystalline brazilein as described herein, wherein said method yields 26 g brazilein per 100 g powdered bark, and said solvent is acetone and water at 1:1 v/v ratio.

In an embodiment of the present disclosure, there is provided a method of detection of nucleic acids in a sample, said method comprising: (a) obtaining a composition as described herein; and (b) contacting said composition with said sample.

In an embodiment of the present disclosure, there is provided a method of detection of nucleic acids as described herein, wherein brazilein is obtained by a process as described herein.

In an embodiment of the present disclosure, there is provided a method of detection of nucleic acids as described herein, wherein said method detects at least 500 pg of DNA in said sample.

In an embodiment of the present disclosure, there is provided a method of detection of nucleic acids as described herein, wherein said method detects at least 40 pg of RNA in said sample.

In an embodiment of the present disclosure, there is provided a method of detection of nucleic acids as described herein, wherein said method is suitable for detection of DNA.

In an embodiment of the present disclosure, there is provided a method of detection of nucleic acids as described herein, wherein said method is suitable for detection of RNA.

In an embodiment of the present disclosure, there is provided a method of detection of nucleic acids as described herein, wherein said method is suitable for detection of ss DNA.

In an embodiment of the present disclosure, there is provided a method of detection of nucleic acids as described herein, wherein said method is suitable for detection of ss RNA.

In an embodiment of the present disclosure, there is provided a method of detection of nucleic acids as described herein, wherein said method is suitable for detection of plasmid DNA.

In an embodiment of the present disclosure, there is provided a method of detection of nucleic acids as described herein, wherein said method is suitable for detection of linearized plasmid DNA.

In an embodiment of the present disclosure, there is provided a method of detection of nucleic acids as described herein, wherein said method is suitable for detection of PCR amplicons.

In an embodiment of the present disclosure, there is provided a method of detection of nucleic acids as described herein, wherein said method is suitable for detection of DNA in live cells.

In an embodiment of the present disclosure, there is provided a method of detection of nucleic acids as described herein, wherein said method is suitable for real time PCR.

In an embodiment of the present disclosure, there is provided a composition as described herein, for use in in-vitro detection of nucleic acids in a sample.

In an embodiment of the present disclosure, there is provided a composition as described herein, for use in in-vitro detection of DNA in a sample.

In an embodiment of the present disclosure, there is provided a composition as described herein, for use in in-vitro detection of RNA in a sample.

In an embodiment of the present disclosure, there is provided a composition as described herein, for use in in-vitro detection of plasmid DNA in a sample.

In an embodiment of the present disclosure, there is provided a composition as described herein, for use in in-vitro detection of linearized plasmid DNA in a sample.

In an embodiment of the present disclosure, there is provided a composition as described herein, for use in in-vitro detection of ss DNA in a sample.

In an embodiment of the present disclosure, there is provided a composition as described herein, for use in in-vitro detection of PCR amplicons.

In an embodiment of the present disclosure, there is provided a composition as described herein, for use in in-vitro detection of real time PCR amplification.

In an embodiment of the present disclosure, there is provided a composition as described herein, for use in in-vivo detection of nucleic acids in a sample.

In an embodiment of the present disclosure, there is provided a composition as described herein, for use in in-vivo detection of DNA in live cells.

In an embodiment of the present disclosure, there is provided a composition as described herein, wherein said composition is non-toxic to cells.

In an embodiment of the present disclosure, there is provided a nucleic acid staining kit comprising a composition, said composition as described herein.

In an embodiment of the present disclosure, there is provided a nucleic acid staining kit as described herein, further comprising an instruction manual.

In an embodiment of the present disclosure, there is provided a nucleic acid staining kit, said kit comprising a composition as described herein, and an instruction manual.

In an embodiment of the present disclosure, there is provided brazilein for use in in-vitro or in-vivo detection of nucleic acids in a sample.

In an embodiment of the present disclosure, there is provided brazilein for use in detection of DNA.

In an embodiment of the present disclosure, there is provided brazilein for use in detection of RNA.

In an embodiment of the present disclosure, there is provided brazilein for use in detection of plasmid DNA.

In an embodiment of the present disclosure, there is provided brazilein for use in detection of PCR amplicons.

In an embodiment of the present disclosure, there is provided brazilein for use in detection of linearized DNA.

In an embodiment of the present disclosure, there is provided brazilein for use in detection of single stranded DNA.

In an embodiment of the present disclosure, there is provided brazilein for use in detection of nucleic acids using confocal microscopy.

In an embodiment of the present disclosure, there is provided brazilein for use in fluorescence activated cell sorting.

In an embodiment of the present disclosure, there is provided brazilein for use in fluorescence in situ hybridization.

In an embodiment of the present disclosure, there is provided brazilein for use in detection of nucleic acids as described herein, wherein brazilein is prepared by a method as described herein.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Example 1

Isolation of Brazilein from *Caesalpinia sappan* Bark Using Various Solvents.

100 grams of shade dried *Caesalpenia sappan* bark tissue was used as a source/raw material for the brazilein extraction. The bark tissue was mechanically powdered and subsequently mixed in distilled water as a solvent (500-2000 ml) and heated (around 80° C.) till the total solution volume was reduced to 20% of the initial volume. This solution was filtered by simple filtration techniques such as by using a filter paper or muslin cloth etc. to obtain a filtrate and a residue. The filtrate was collected and left aside for 3 to 5 days at room temperature (22-30° C.) for oxidation of brazilin to brazilein. The solvent was removed by evaporation either by heating it or by leaving it aside for a period of 3 to 5 days, allowing complete oxidation of brazilin to brazilein. During this period, oxidized brazilein also dried up forming a crystalline powder. In order to maximize brazilein extraction, the residue obtained post filtration was subjected to repeated extraction as mentioned above to obtain a second filtrate. This repeated extraction was carried out 3-5 times to obtain multiple filtrates, which were subsequently pooled for isolation of oxidized brazilein.

The process as mentioned above was also carried out by substituting the solvent (water as given above) with (a) methanol; or (b) a mixture of methanol and ethanol at v/v ratio of 1:1; or (c) a mixture of methanol and water at v/v ratio of 4:1; or (d) a mixture of ethanol and water at v/v ratio of 4:1; or (e) ethanol; or (f) acetone; or (g) a mixture of acetone and methanol at v/v ratio of 1:1; or (h) a mixture of acetone and water at v/v ratio of 1:1.

Brazilein yield post isolation using various processes is as given below in Table 1. Table 1 also provides the heating time. The powdered bark to solvent w/v ratio was kept at 20:1. It is understood that the heating time will vary depending upon the solvent volume and selection.

TABLE 1

| Solvent | Bark powder | Yield/100 gm | Time at 80° C |
|---|---|---|---|
| methanol | 100 g | 20 g | 4-5 h |
| methanol:ethanol (1:1) | 100 g | 21.5 g | 4 h |
| methanol:water (4:1) | 100 g | 19 g | 5-6 h |
| ethanol:water (4:1) | 100 g | 22 g | 5-6 h |
| water | 100 g | 18 g | 12 h |
| ethanol | 100 g | 25 g | 4-5 h |
| acetone | 100 g | 28.5 g | 3-4 h |
| methanol:acetone (1:1) | 100 g | 25 g | 3-4 h |
| acetone:water (1:1) | 100 g | 26 g | 3-4 h |

As seen in Table 1 above, the yield using various solvents ranges from 18-28.5 g per 100 g of powdered bark. Maximal yield can be seen in the case of acetone extract of brazilein, whereby 100 g of powdered bark provides 28.5 g of brazilein.

Figure 1A:
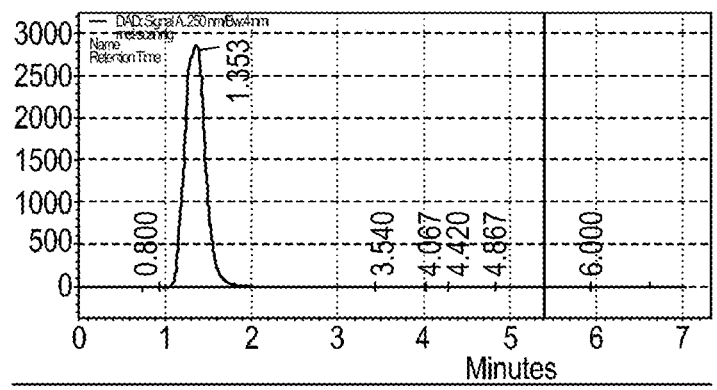
FIG. 1a depicts the single peak in a HPLC chromatogram corresponding to brazilein, in accordance with an embodiment of the present disclosure.
Figure 1B:
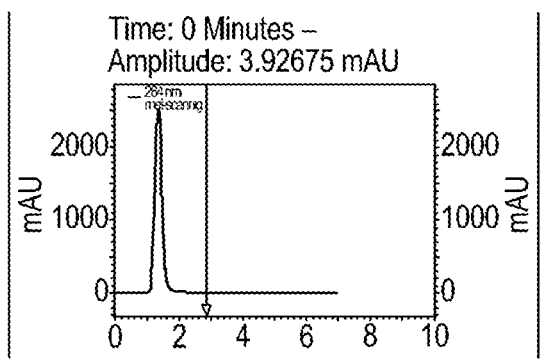
FIG. 1b depicts the dominant peak in GC-MS confirming the purity of extracted brazilein, in accordance with an embodiment of the present disclosure.
Figure 1C:
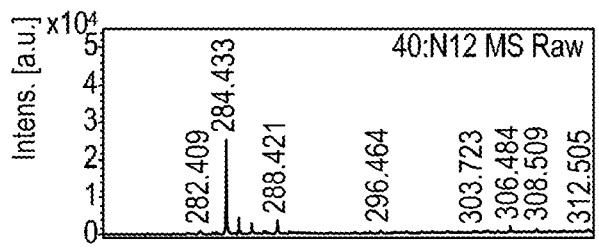
FIG. 1c depicts the mass spectrometric profile showing a peak of 284 mw that corresponds to brazilein, in accordance with an embodiment of the present disclosure.

Purity and heat stability of brazilein was confirmed with HPLC (FIG. 1a, water extract of brazilein) and GC analysis (FIG. 1b, methanol extract of brazilein) using a reference volume of 20 ul. The purified crystals where re-dissolved in the solvent and subjected to HPLC, GC-MS and MS-MS (FIG. 1c), that gave a single major peak corresponding to the molecular weight of brazilein. Area integration of each peak in the HPLC profile was used to estimate the product concentration. The structure of the purified compound was confirmed by GC and Mass spectral analysis as shown.

Example 2

Fluorescent Emission Spectra of Brazilein

Figure 2A:
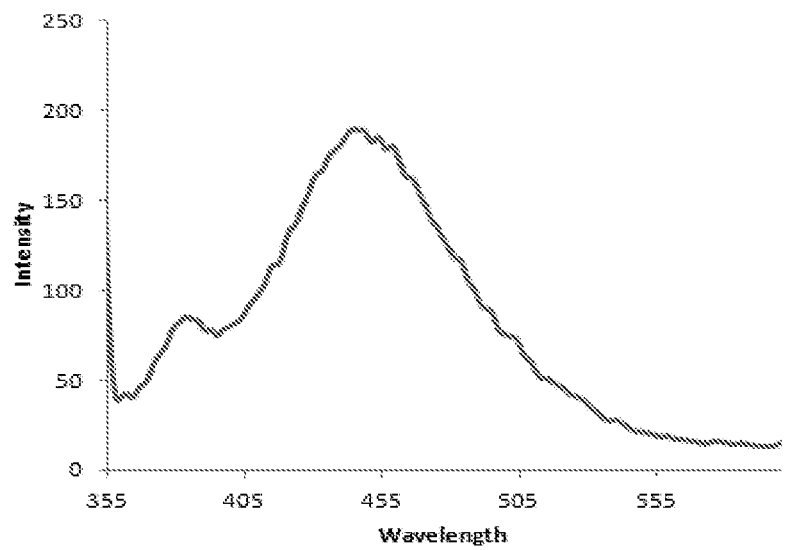
FIG. 2a depicts the fluorescence emission spectra with emission maximum at 450 nm (excitation wavelength 340 nm) of the methanol extract, in accordance with an embodiment of the present disclosure.
Figure 2B:
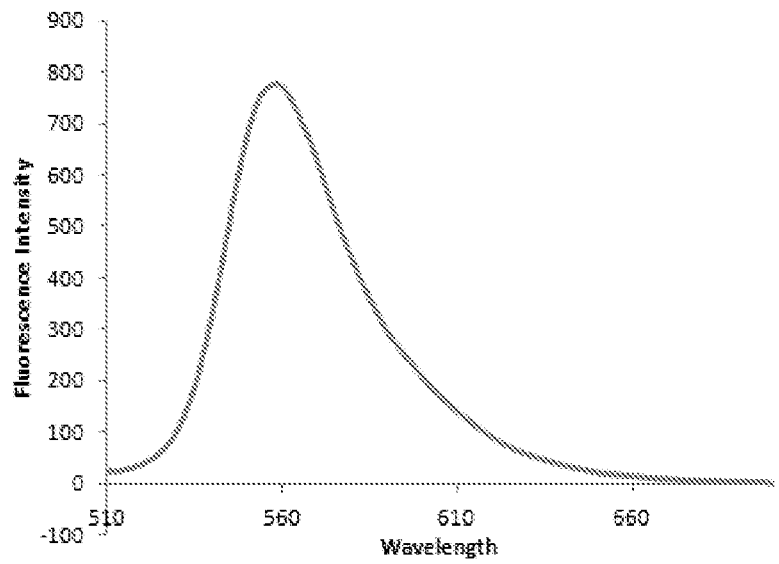
FIG. 2b depicts the fluorescence emission spectra with emission maximum at 560 nm (excitation wavelength 491 nm) of the methanol extract, in accordance with an embodiment of the present disclosure.

As seen in FIG. 2a, the methanolic extract of brazilein has a fluorescence emission spectra with emission maximum at 450 nm (excitation wavelength 340 nm). FIG. 2b shows that the methanolic extract of brazilein has fluorescence emission spectra with emission maximum at 560 nm (excitation wavelength 491 nm). These data suggest that nucleic acid detection using brazilein can be effectively captured using existing technologies such as UV transilluminators, and gel documentation systems. The fluorescence spectra can also find application in in vivo imaging and confocal microscopy.

Example 3

Nucleic Acid Staining Activity of Brazilein

Figure 3A:
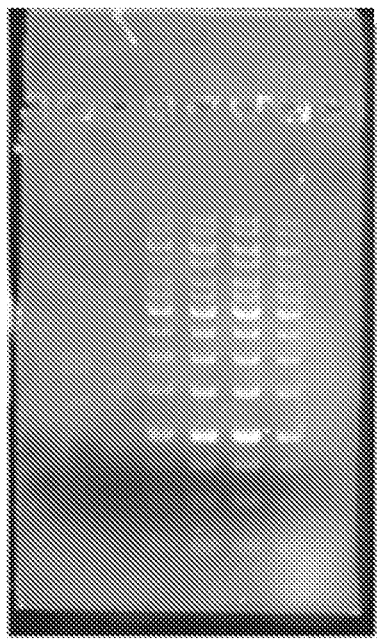
FIG. 3a depicts the staining of DNA at various concentrations by ethidium bromide, in accordance with an embodiment of the present disclosure.
Figure 3B:
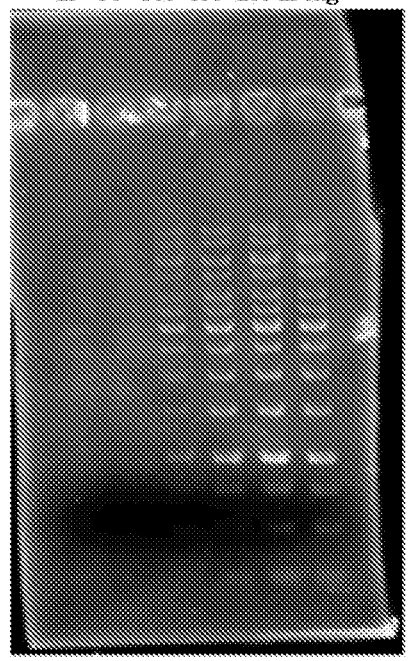
FIG. 3b depicts the staining of DNA at various concentrations by SYBR® Gold, in accordance with an embodiment of the present disclosure.
Figure 3C:
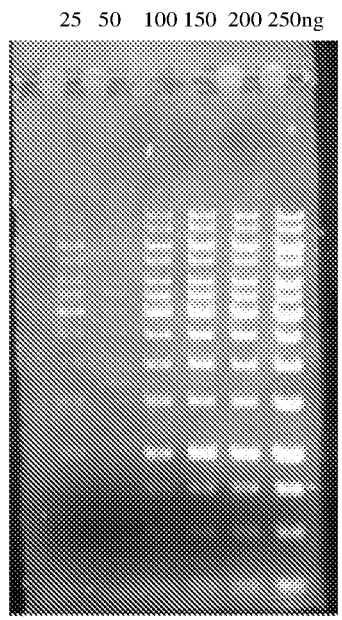
FIG. 3c depicts the staining of DNA at various concentrations by methanolic extract of brazilein, in accordance with an embodiment of the present disclosure.
Figure 3D:
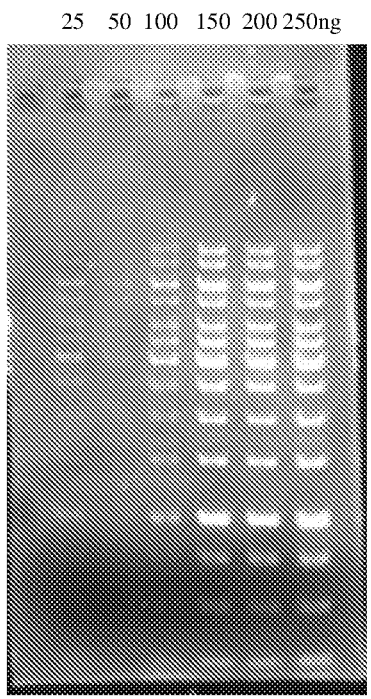
FIG. 3d depicts the staining of DNA at various concentrations by ethanolic extract of brazilein, in accordance with an embodiment of the present disclosure.

In order to ascertain the utility of brazilein in fluorescence aided visualization of DNA, various amounts of DNA ladder ranging from 50-250 ng were stained with ethidium bromide (EtBr) (50 μg/50 ml of staining volume) (FIG. 3a), or SYBR® Gold (FIG. 3b), or tm (methanolic extract of brazilein) (1 mM brazilein) (FIG. 3c), or te (ethanolic extract of brazilein) (1 mM brazilein) (FIG. 3d). It can be inferred from FIGS. 3a-d that tm or te stains DNA more brightly than EtBr or SYBR® Gold at DNA concentrations of 100-250 ng. However, te and tm are able to effectively stain DNA concentrations of 25-50 ng also, which are not stained by EtBr or SYBR® Gold, which is suggestive of the fact that brazilein at the concentrations tested is not only effective in staining DNA for fluorescent visualization of DNA, but is more sensitive than EtBr or SYBR® Gold at the concentrations tested.

Figure 3E:
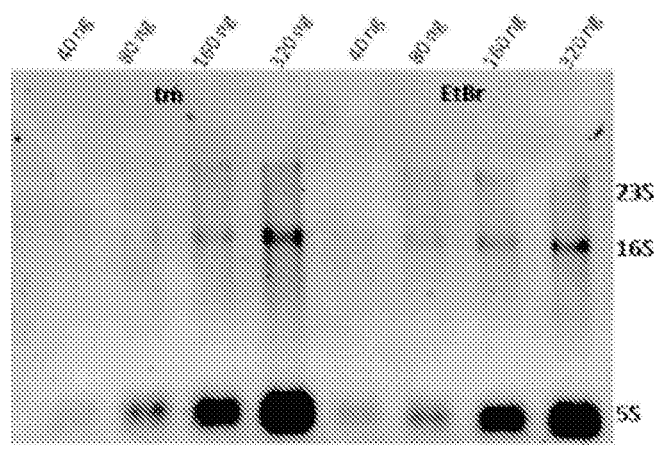
FIG. 3e depicts the staining ability of brazilein on RNA, in accordance with an embodiment of the present disclosure.

Brazilein (tm) can also stain RNA (minimum RNA concentration of 40 ng, up to 320 ng) as shown in FIG. 3e. Further, as seen in FIG. 3e, compared to the staining sensitivity of ethidium bromide, it can be seen that tm stains (1 mM) RNA more intensely (RNA was isolated from E. coli using TRIZOL method; A260/A280=2.04; quantity=3000 ng/ml).

Figure 3F:
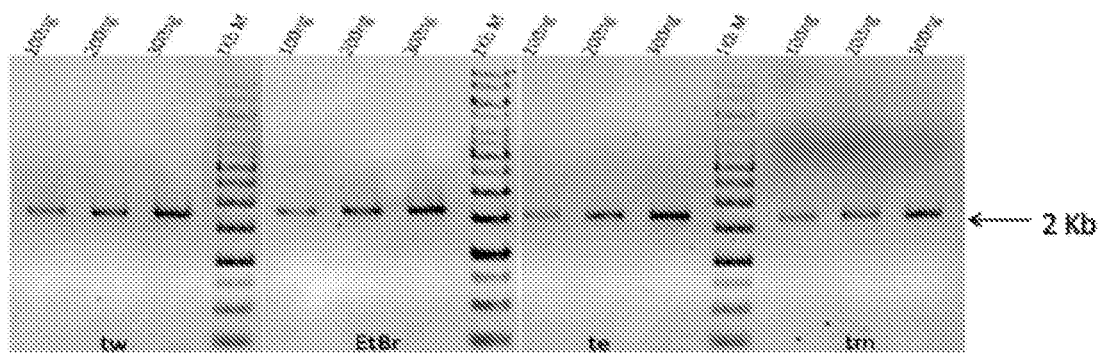
FIG. 3f depicts the staining ability of brazilein on PCR amplicons, in accordance with an embodiment of the present disclosure.

Various extracts of brazilein (1 mM/50 ml of staining volume) (tw: water extract of brazilein; te: ethanolic extract of brazilein; tm: methanolic extract of brazilein) can also efficiently stain DNA fragments generated from by PCR as shown in FIG. 3f. As seen in FIG. 3f, various extracts of brazilein (tw, or te, or tm) are able to stain (at par) a 2 kb amplicon at concentrations ranging from 100-300 ng, which is comparable to the staining effect of ethidium bromide.

Figure 4A:
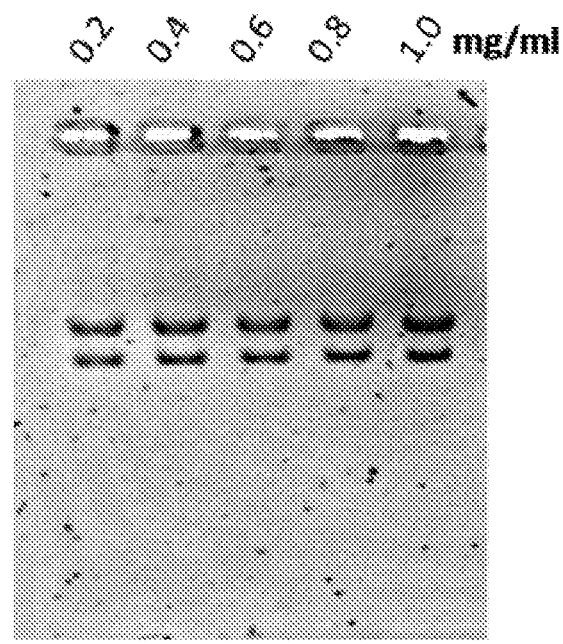
Figure 4B:
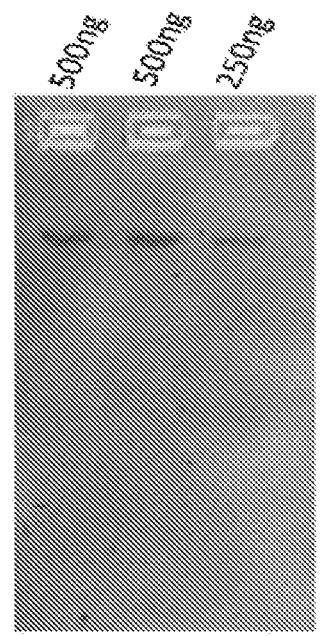
Figure 4C:
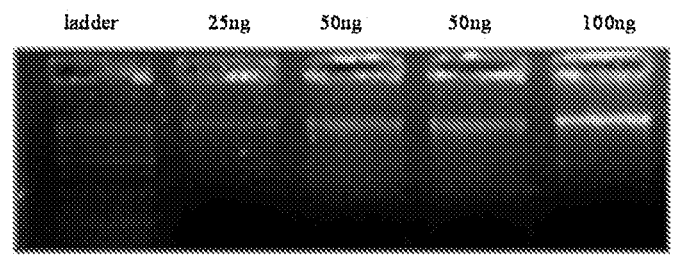
Figure 4D:
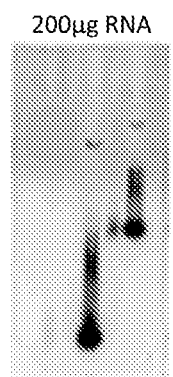

Brazilein can also stain various types/forms of nucleic acids, as show in FIGS. 4a-c. FIG. 4a shows staining of plasmid DNA at DNA concentrations ranging from 0.2-1 mg/ml. FIG. 4b shows that brazilein can effectively stain genomic DNA (250-500 ng tested). Brazilein can also stain ssDNA as show in FIG. 4c. Further, brazilein (1 μl of 1 mM brazilein stock solution/50 ml of staining solution) can also stain RNA as shown in FIG. 4d (200 μg RNA per lane. The difference in the size is due to two different RNA preparations). Amount of brazilein dye used was 1 mM.

Example 4

Staining Sensitivity of Brazilein

The staining sensitivity of brazilein in an agarose gel was determined by staining various amounts of DNA fragments ranging from 200 pg-4 ng in an agarose gel using brazilein extracted using methanol (tm), ethanol (te), or water (tw) as described previously in the present disclosure.

As seen in FIG. 5a, te (1 mM) (ethanol extract of brazilein), and tw (water extract of brazilein) is able to detect 1 ng DNA. However, the methanol extract of brazilein (tm) is unable to detect 1 ng of DNA.

At lower DNA concentrations, ranging from 200-800 pg (FIG. 5b), bands were visible for DNA concentration as low as 400 pg for tm, te, or tw, but were not reliable stained at lower concentrations, suggesting that the sensitivity of the dye is around 200 pg.

Example 5

Fluorescence Comparison of Brazilein and Ethidium Bromide (EtBr)

In order to ascertain and establish the superiority of brazilein as a DNA visualizing agent over EtBr, which is a widely and commonly used compound, concentration dependent fluorescent of various brazilein extracts, and EtBr was evaluated.

FIG. 6a shows the fluorescence intensity of EtBr at concentrations ranging from 1-20 μM, results of which are presented in tabulated format in Table 2 below.

TABLE 2

| EtBr concentration (μM) | Fluorescence intensity (AU) |
|---|---|
| 1 | <20 |
| 5 | ~60 |
| 10 | ~10 |
| 15 | ~180 |
| 20 | ~230 |

FIG. 6b shows the fluorescence intensity of methanolic extract of brazilein at concentrations ranging from 1-20 μM, results of which are presented in tabulated format in Table 3 below.

TABLE 3

| EtBr concentration (µM) | Fluorescence intensity (AU) |
| --- | --- |
| 1 | <50 |
| 5 | ~200 |
| 10 | ~380 |
| 15 | ~520 |
| 20 | ~800 |

FIG. 6c shows the fluorescence intensity of ethanolic extract of brazilein at concentrations ranging from 1-20 µM, results of which are presented in tabulated format in Table 4 below.

TABLE 4

| EtBr concentration (µM) | Fluorescence intensity (AU) |
| --- | --- |
| 1 | <50 |
| 5 | ~150 |
| 10 | ~350 |
| 15 | ~500 |
| 20 | ~650 |

As seen from FIGS. 6a-c, and Tables 2-4, it can be readily appreciated that brazilein at comparable concentrations to ethidium bromide gives a significantly higher fluorescent intensity, suggesting that brazilein is a superior alternative to ethidium bromide.

Example 6

Effect of pH on Brazilein Fluorescence

In order to determine the application of brazilein as a dye under various pH conditions, the effect of varying pH ranging from 5-10 on fluorescence intensity was studied (FIG. 7a-f).

FIG. 7a depicts the fluorescent intensity of various concentrations (5-25 µM) of extract of brazilein (te) at pH of 5. As seen in FIG. 7a, at pH 5, fluorescence intensity of te is very poor at all concentrations tested, suggesting that brazilein cannot be reliably used as an indicator dye at pH of 5 at least at the various concentrations tested.

FIG. 7b depicts the fluorescent intensity of various concentrations (5-25 µM) of ethanolic extract of brazilein (te) at pH of 6. As seen in FIG. 7b, at pH 6, maximal intensity of about 40 AU is observed for te at concentration of 25 µM. te at 20 µM concentration shows a fluorescence intensity of about 30 AU, while the rest show intensity <20 AU.

FIG. 7c depicts the fluorescent intensity of various concentrations (5-25 µM) of ethanolic extract of brazilein (te) at pH of 7. As seen in FIG. 7c, te at 25 µM concentration shows intensity of about 110 AU, while te at concentration of 20 µM concentration shows intensity of about 80 AU.

FIG. 7d depicts the fluorescent intensity of various concentrations (5-25 µM) of ethanolic extract of brazilein (te) at pH of 8. As seen in FIG. 7d, te at 25 µM concentration shows intensity of about 250 AU, while te at concentration of 20 µM shows intensity of about 180 AU. te at concentration of 15 µM shows intensity of about 120 AU.

FIG. 7e depicts the fluorescent intensity of various concentrations (5-25 µM) of ethanolic extract of brazilein (te) at pH of 9. As seen in FIG. 7e, te at 25 µM concentration shows intensity of about 450 AU, while te at concentration of 20 µM shows intensity of about 350 AU. te at concentration of 15 µM shows intensity of about 250 AU, while te at concentration of 10 µM shows intensity of about 150 AU.

FIG. 7f depicts the fluorescent intensity of various concentrations (5-25 µM) of ethanolic extract of brazilein (te) at pH of 10. As seen in FIG. 7f, te at concentration of 25 µM shows intensity of about 200 AU, while te at concentration of 20 µM shows intensity of about 150 AU, and te at concentration of 15 µM shows intensity of about 110 AU.

Overall, based on FIGS. 7a-f, it can be appreciated that brazilein (te) is a suitable fluorescent dye for use over a wide range of pH, ranging from 5-10, at concentration of 20-25µM. Brazilein is most effective at pH in the range of 7-9, whereby a high fluorescent intensity is observed even at lower concentrations as tested.

Example 7

Enhanced Fluorescent Activity of Brazilein

It was surprisingly and unexpectedly found that the presence of certain molecules such as glycerol, or sodium salt or magnesium salt, the fluorescence intensity is enhanced. As seen in FIG. 8, while 5 µM methanolic extract of brazilein (tm) gave a maximum fluorescent intensity of about 200 AU, the combination of tm (methanolic extract of brazilein and glycerol, wherein wt % age is about 25%, and brazilein wt % is about 0.00003%), the fluorescent intensity observed was about 550 AU, which is about 2.75 fold more than the effect of brazilein alone. This observed enhancement is unexpected and surprising as glycerol alone does not have any significant fluorescent activity for detection of DNA.

Various metal ions were also evaluated for their effect on fluorescent intensity of brazilein as metal ions are known to act as adjuvants, and enhance fluorescence in molecules by forming stable complexes or by altering charge. As seen in FIG. 9, of the various metal ions tested at concentration of 100 µM, along with brazilein at concentration of (1 mM), it was observed that except for sodium, and magnesium, none of the other ions tested enhance the fluorescent activity of tm (methanolic extract of brazilein). In fact, it can be appreciated that the presence of the other ions acts to inhibit the fluorescent intensity of brazilein.

As seen more clearly in FIG. 10, presence of sodium ions (sodium chloride) at a concentration of 10 µM, whereby brazilein (tm: methanolic extract of brazilein) concentration is 1 mM, the fluorescent intensity is about 3 fold more. Similarly, in the presence of magnesium ions (magnesium sulfate) as shown in FIG. 11, the fluorescent intensity is more than about 4 fold compared to the intensity generated by tm (methanolic extract of brazilein) alone. Sodium or potassium are not known impart any significant fluorescent properties which may aid in detection of nucleic acids These figures collectively show that the presence of glycerol or sodium or potassium ions, unexpectedly and surprisingly result in an apparent synergistic increase in fluorescent intensity of brazilein.

Example 8

Cell Toxicity of Brazilein

In order to evaluate the safety of brazilein as a suitable alternative to ethidium bromide, which is a mutagen, various concentrations of brazilein or in combination with glycerol, or metal ions were tested on HeLa cell viability.

MTT assay was performed as per standard protocol. Foremost, cultured HeLa cells were collected in medium after trypsinization. Culture was diluted with another 20 ml media to reduced the cell nos. approximately to 10000 cells per 100 µL. Cells were counted using hemocytometer. 100 µL of culture were taken in each wells of 96-well plate and allowed for adherence overnight. Next day, HeLa cells were treated with different concentrations of brazilein (0.152-10 µM) for 24 h, followed by MTT (3-(4-5 dimethylthiozol-2-yl) 2-5diphenyl-tetrazolium bromide) treatment (4 mg/mL) for 4 h at 37° C. Appearance of purple color crystal were observed, gently the medium from the wells was aspirated. 200 µL of DMSO was added to dissolve the crystals. After 15 minutes of incubation in dark, absorbance measurements were taken in a UV-visible spectrophotometer at 540 nm. Percent cell viability was plotted for each set (untreated and treated) against concentration of dye used.

In FIG. 12a, tw refers to water extract of brazilein, tw (gly) refers to water extract of brazilein and glycerol, tw+Na refers to water extract of brazilein and sodium salt, while tw+Mg refers to water extract of brazilein and magnesium salt. As seen in FIG. 12a, the various combinations were tested at concentrations ranging from 0.156-10 µM. It can be observed that even at the highest concentration tested, (10 µM), all of the combinations tested are safe, and do not significantly affect cell viability.

In FIG. 12b, tm refers to methanolic extract of brazilein, tm (gly) refers to methanolic extract of brazilein and glycerol, tm+Na refers to methanolic extract of brazilein and sodium salt, while tm+Mg refers to methanolic extract of brazilein and magnesium salt. As seen in FIG. 12b, the various combinations were tested at concentrations ranging from 0.156-10 µM. It can be observed that even at the highest concentration tested, (10 µM), all of the combinations tested are safe, and do not significantly affect cell viability. The data as shown in FIG. 12a-b show that brazilein is a safe dye, which can be used without any cell toxic effects, at the concentrations tested.

Example 9

Method of Staining of Biological Samples

Brazilein composition (stain) as described in the present disclosure may be used for staining of DNA in an agarose gel for visualization in a uv transilluminator system (UV). Staining can be carried out by either directly loading the stain with the DNA prior to loading; or adding the stain to agarose prior to gelation; or adding stain to gel post electrophoresis. It was observed that when the stain (500 ng/ml) is added to the gel after DNA migration, visualization can be carried out within 30-60 seconds of incubation, which is significantly quicker than ethidium bromide, which takes anywhere from 10-30 minutes for effective DNA binding. The optimum stain amount required to bind DNA when added directly with the DNA prior to loading was found to be 50 ng/250 pgDNA.

Example 10

Fluorescence/Confocal Microscopy

Fluorescence microscopy was used for analyzing the live cell staining with brazilein in onion epidermal cells. Briefly, onion peel was removed gently and divided into two parts, permeabilized and non-permeabilized cells. For non-permeabilization, cells were soaked in water for 10 minutes, whereas for permeabilization, cells were soaked in formalin for 10 minutes. The peels were taken and dipped in different concentrations of methanol extract of brazilein (500 nM-1 mM) and allowed to incubate in dark for 15 minutes. The incubated samples were taken and placed on glass slide, coverslip was placed over it and sealed to avoid drying of sample. Slides were visualized under fluorescence microscope. As seen in FIG. 13, 10 µM brazilein is able to stain nuclei of onion epidermal cells, indicating that brazilein can penetrate cells, and uniformly and reliably stain nuclei of cells specifically with minimal background. It was further observed that cell permeabilization is not an essential requirement as brazilein is able to stain nuclei in non-permeabilized cells also. Further, while all extract of brazilein (water, ethanol, acetone, or combinations thereof as described previously) were able to stain nuclei in cells, the representative image of FIG. 13 depicts methanolic extract of brazilein as it showed best results. with regard to concentration of brazilein required for staining of nuclei of cells, it was deduced that 10 µM brazilein is optimum. Concentrations below 10 µM give faint fluorescent signal, while concentrations higher than 10 µM give higher noise and background.

Example 11

Fluorescence Activated Cell Sorting (FACS)

FACS analysis was used to analyze entry of dye into fixed and un-fixed cells, as applicable in cell cycle studies. *Salmonella* cells were harvested in the appropriate manner using trypsin. The trypsinized cells in the cell culture was centrifuged at 1300 rpm for 5 minutes to pellet down the cells. To fix the cells, cold 70% ethanol was added to the cells. Fixing was done for 30 min at 4° C. 200 µl of brazilein (methanolic extract) (from 50 µg/ml stock solution). The cells were spun again at 1300 rpm for 5 minutes at room temperature and the supernatant was decanted. To permeabilize the cells, a mixture of 1× phosphate buffered saline (PBS) and saponin (0.1%) was added and incubated for 5 minutes. Cells were centrifuged and washed with PBS was given to cell to remove saponin. The cells were treated with 1 µg/mL working concentration of ribonuclease (100 µg/mL) to ensure only DNA is stained not RNA. The same process was followed for un-fixed cells except for addition of ethanol and saponin to cells. Different concentrations of brazilein (500 nM-10 µM) was added and incubated for 15 minutes at room temperature and tubes were subjected for FACS analysis. The data as show in FIG. 14b reveals that brazilein (5 µM) (saturation concentration) has entered 96.8% of total live bacterial cells, thus displaying efficacy of using brazilein for FACS studies (FIG. 14a are control cells, which have not been treated with any dye).

Example 12

Live-Cell Staining Using Brazilein

In order to determine the utility of brazilein in staining of live cells, yeast cells were stained with 1 mM brazilein and observed under confocal microscope at 40× magnification. The cells were visualized under various filters to ascertain optimal visualization conditions. As show in FIG. 15a, the green filter shows faint visualization of the nuclear material of the cells. FIG. 15b is a phase contrast image of the cells. FIG. 15c depicts the cells visualized using a red filter, while FIG. 15d depicts the cells using a far red filter. From FIGS. 15a, c, and d, it suggests that red filter is most appropriate to visualize cells (nuclear material). FIG. 15e is a merged image of 15a-d. Overall, these set of figures reveal that brazilein can be used as a dye to stain nuclei in live cells, and can be visualized in red channel of confocal microscope.

Example 13

Fluorescence In-Situ Hybridization (FISH)

Brazilein can also be used for FISH (standard protocol known in the art) as shown in FIG. 16. As inferred from FIG. 16, 10 μM brazilein can effectively stain chromosomes of human cells.

Overall, the present disclosure provides brazilein for use as a dye for visualization of nucleic acids, such as DNA, and RNA, using a variety of methods such as gel staining, live cell staining, FISH, FACS, and fluorescence microscopy. The present disclosure also provides a cost and time efficient method of solvent mediated extraction of brazilein from bark of *Caesalpinia sappan*, which has not been reported in the prior art to be a usable source. Additionally, surprisingly, and unexpectedly, it was also observed, and disclosed herein that brazilein in the presence of certain additives such as glycerol, DMSO, or metal salts, the fluorescent intensity of brazilein is synergistically enhanced. Brazilein as a nucleic acid dye as disclosed in the instant specification is non-toxic, highly sensitive, can be used in live cells for DNA visualization, and a is viable and superior alternative than other stains such as ethidium bromide, which is a known mutagen, or stains such as SYBR® Gold, which is also a mutagen, and is expensive. The composition of the present disclosure is therefore a safe and more sensitive alternative.

We claim:

1. A composition for detection of nucleic acids comprising:
   a. brazilein((6aS,11bR)-7,11b-Dihydro-6H-indeno[2,1-c]chromene-3,6a,9,10-tetrol);
   b. at least one solvent selected from the group consisting of methanol, ethanol, acetone, and combinations thereof; and
   c. at least one compound selected from the group consisting of glycerol, sodium chloride, magnesium sulfate, dimethyl sulfoxide, and combinations thereof.

2. The composition as claimed in claim 1, wherein said solvent weight percentage in said composition is in quantity sufficient to dissolve brazilein.

3. The composition as claimed in claim 1, wherein brazilein weight percentage in said composition is in the range of 0.000284-0.0284%.

4. The composition as claimed in claim 1, wherein sodium chloride or magnesium sulfate weight percentage in said composition is in the range of 0.0001%-0.001%.

5. The composition as claimed in claim 1, wherein glycerol weight percentage in said composition is in the range of 25.2-37.8%.

6. The composition as claimed in claim 1, wherein dimethyl sulfoxide weight percentage in said composition is in the range of 70-90%.

7. The composition as claimed in claim 1, wherein the composition comprises sodium chloride or magnesium sulfate, and wherein brazilein to sodium chloride or magnesium sulfate w/w ratio in said composition is in the range of 1:0.0035-1:3.52 .

8. The composition as claimed in claim 1, wherein the composition comprises glycerol, and wherein brazilein to glycerol w/w ratio in said composition is in the range of 1:887-1:133098.

9. The composition as claimed in claim 1, wherein the composition comprises dimethyl sulfoxide, and wherein brazilein to dimethyl sulfoxide w/w ratio in said composition is in the range of 1:2464-1:316901.

10. A composition as claimed in claim 1 for use in in-vitro or in-vivo detection of nucleic acids in a sample.

11. A nucleic acid staining kit comprising a composition as claimed in claim 1.

12. A method of detection of nucleic acids in a sample, said method comprising:
    a. obtaining a composition as claimed in claim 1; and
    b. contacting said composition with said sample.

13. The method as claimed in claim 12, wherein brazilein is obtained by a process comprising:
    a. obtaining bark from *Caesalpinia sappan;*
    b. processing said bark to obtain powdered bark;
    c. contacting said powdered bark with at least one solvent to obtain a first mixture;
    d. subjecting said first mixture to a temperature in the range of 20-90° C. until the volume of the first mixture is reduced by 80-95% to obtain a second mixture;
    e. filtering the second mixture to obtain:
       i. a filtrate comprising mixture of brazilin and brazilein; and
       ii. a residue; and
    f. contacting said filtrate to air or at least one oxidizing agent at a temperature in the range of 22-85° C. to evaporate residual solvent to obtain brazilein in crystalline form.

14. The method as claimed in claim 12, wherein said method detects at least 40 pg of nucleic acids in said sample.

* * * * *